(12) United States Patent
Vuillerme et al.

(10) Patent No.: US 10,576,326 B2
(45) Date of Patent: Mar. 3, 2020

(54) METHOD AND SYSTEM FOR MEASURING, MONITORING, CONTROLLING AND CORRECTING A MOVEMENT OR A POSTURE OF A USER

(71) Applicants: ASSOCIATION POUR LA RECHERCHE DEVELOPPEMENT DES METHODES ET PROCESSUS INDUSTRIELS (ARMINES), Paris (FR); UNIVERSITE GRENOBLE ALPES, St. Martin d'Hères (FR); INFOMATIQUE DE SECURITE, Montceau les Mines (FR)

(72) Inventors: Nicolas Vuillerme, St. Martin d'Hères (FR); Céline Franco, Le Fontanil-Cornillon (FR); Bruno Diot, Mercurey (FR); Quentin Mourcou, Bourgoin-Jallieu (FR); Anthony Fleury, Douai (FR)

(73) Assignees: Association Pour la Recherche Developpement des Methodes et Processus Industriels—A.R.M.I.N.E.S., Paris (FR); Universite Grenoble Alpes, Saint Martin d'Heres (FR); Informatique de Securite, Montceau les Mines (FR)

( * ) Notice: Subject to any disclaimer, the term of this patent is extended or adjusted under 35 U.S.C. 154(b) by 173 days.

(21) Appl. No.: 15/527,171

(22) PCT Filed: Nov. 20, 2015

(86) PCT No.: PCT/FR2015/053157
§ 371 (c)(1),
(2) Date: May 16, 2017

(87) PCT Pub. No.: WO2016/079452
PCT Pub. Date: May 26, 2016

(65) Prior Publication Data
US 2017/0354843 A1  Dec. 14, 2017

(30) Foreign Application Priority Data
Nov. 20, 2014  (FR) .................................... 14 61233

(51) Int. Cl.
*G09B 5/02*  (2006.01)
*A63B 24/00*  (2006.01)
(Continued)

(52) U.S. Cl.
CPC ........ *A63B 24/0003* (2013.01); *A61B 5/0002* (2013.01); *A61B 5/112* (2013.01);
(Continued)

(58) Field of Classification Search
CPC ................................................. A63B 24/0003
(Continued)

(56) References Cited

U.S. PATENT DOCUMENTS

| 7,867,140 B2 | 1/2011 | Chiari et al. |
| 2010/0110169 A1 | 5/2010 | Zerkin |

(Continued)

FOREIGN PATENT DOCUMENTS

| EP | 2231013 A2 | 9/2010 |
| WO | WO-2008/132324 A1 | 11/2008 |
| WO | WO-2009/090200 A2 | 7/2009 |

OTHER PUBLICATIONS

Karime, A. et al., "Determining Wrist Reference Kinematics Using a Sensory-mounted Stress Ball," Robotic and Sensors Environments (ROSE), IEEE International Symposium, Nov. 16, 2012, 6 pages.
(Continued)

*Primary Examiner* — Kesha Frisby

(74) *Attorney, Agent, or Firm* — Harness, Dickey & Pierce, PLC

(57) ABSTRACT

A method for measuring, monitoring, controlling, evaluating and correcting proprioceptive and/or postural and/or locomotor and/or motor and/or spatial orientation abilities of a user, includes measuring and processing in order to detect an effective movement or an effective posture of the user; comparing the effective movement or the effective posture to a theoretical movement or a theoretical posture; providing biological feedback in order to allow the user to correct his effective movement or his effective posture with respect to the theoretical movement or the theoretical posture; calculating and storing a score; transmitting the score to a third party in order to allow the latter to monitor the performances of the user; and automatically or non-automatically updating a level of difficulty.

13 Claims, 2 Drawing Sheets

(51) Int. Cl.
| | |
|---|---|
| *A61B 5/00* | (2006.01) |
| *A61B 5/11* | (2006.01) |
| *G09B 5/04* | (2006.01) |
| *G09B 19/00* | (2006.01) |

(52) U.S. Cl.
CPC .......... *A61B 5/1116* (2013.01); *A61B 5/1122* (2013.01); *A61B 5/4023* (2013.01); *A61B 5/486* (2013.01); *A61B 5/6898* (2013.01); *A61B 5/725* (2013.01); *A61B 5/746* (2013.01); *G09B 5/02* (2013.01); *G09B 5/04* (2013.01); *G09B 19/00* (2013.01); *A61B 5/45* (2013.01); *A61B 2562/0219* (2013.01); *A61B 2562/0223* (2013.01)

(58) Field of Classification Search
USPC ........................................................ 434/247
See application file for complete search history.

(56) References Cited

U.S. PATENT DOCUMENTS

| | | |
|---|---|---|
| 2011/0021318 A1 | 1/2011 | Lumsden et al. |
| 2011/0137213 A1 | 6/2011 | Caulfield et al. |

OTHER PUBLICATIONS

Karime, A. et al., "A Fuzzy-Based Adaptive Rehabilitation Framework for Home-Based Wrist Training," IEEE Transactions on Instrumentation and Measurement, IEEE Service Center, Piscataway, NJ, Jan. 1, 2014, 10 pages.

Ayub, S. et al., "A Sensor Fusion Method for Smart phone Orientation Estimation," Proceedings of the 13th Annual Post Graduate Symposium on the Convergence of Telecommunications, Networking and Broadcasting, Liverpool, Jun. 30, 2012, 6 pages.

METHOD AND SYSTEM FOR MEASURING, MONITORING, CONTROLLING AND CORRECTING A MOVEMENT OR A POSTURE OF A USER

CROSS-REFERENCE TO RELATED APPLICATIONS

This application is a National Phase Entry of International Patent Application No. PCT/FR2015/053157, filed on Nov. 20, 2015, which claims priority to French Patent Application Serial No. 1461233, filed on Nov. 20, 2014, both of which are incorporated by reference herein.

TECHNICAL FIELD

The present invention relates to the field of the measurement, of the monitoring, of the control and of the correction of a movement or a posture carried out by a user (human or animal). Within the scope of the present invention, by "movement" is meant the displacement of a body relatively to a reference system of the space and at a determined moment, this displacement being able to be zero (immobile body) or non-zero (mobile body). More specifically, the present invention relates to a method and to a system for evaluating the monitoring, the correcting, the retraining and the training of proprioceptive and/or postural and/or locomotor and/or motor and/or spatial orientation abilities of a user.

By "movement" within the scope of the present invention, is meant the displacement of a point (or of a set of points), of one (or several) body segment(s) of the user (the torso, the femur, the foot, the tibia/fibula, hip, arm, forearm, etc.) in space over time, this displacement being able to be zero (immobile point) or non-zero (mobile point). In the case of a point, such a movement may be defined by a sequence of positions in space taken during time, and for a sequence of displacement speeds between two successive positions of the sequence of positions. Commonly, a movement is represented by a set of vectors (for example "velocity vector" or "orientation vector") which each define the displacement of a point relatively to a fixed reference system in space and at a determined instant.

The invention advantageously finds many applications, notably in specialties associated with rehabilitation:
  of elderly persons and/or in a handicapped situation,
  of persons having been subject to trauma or to a surgical operation.
It may also be used in more recreational applications such as sports training or wellness activities.

BACKGROUND

Whether this is caused by ageing, accident, an injury or a trauma, the present invention gives the possibility of assisting a user by correcting his/her movements in order to:
  help him/her recover a body function which was altered (for example in order to again find the use of a hand after repair surgery), or at the very least
  to teach him/her to adapt to a new condition (teach a person amputated of a lower limb to walk with a prosthesis, a person victim of a stroke, etc.).
Devices and assumed methods are known for helping a user to recover a body function. Document WO 2008/132324 describes a method for measuring and correcting the postural vertical position of a human being. This device comprises a camera, a viewing screen and processing means. The operating principle of such a device is the following:
  the user is installed in a sitting position without any back seat,
  two markers are positioned in his back along his/her spine,
  the camera is installed behind the user so as to acquire images of his/her back,
  the viewing screen is installed in front of the user so that he/she may observe the images displayed on said screen, finally
  the processing means are connected to the camera and to the display screen.
Once the installation is finished, the camera is enabled in order to acquire images of the back of the user. These images are transmitted to the processing means giving the possibility of estimating a tilt of the patient's back relatively to the vertical. The processing means then control the display on the viewing screen:
  of a schematic illustration of the user,
  of his/her tilt relatively to the vertical, modelled by the line segment between both markers, and
  of a deviation angle value of said tilt.
Such a device has many drawbacks. On the one hand, the installation of the device on the whole is tedious and may not be applied by the user him/herself. Indeed, the installation of markers in the user's back and the positioning of the camera requires the presence of a person for assisting the user. Further, the complexity of setting into place the device makes the use of the latter prohibitive. The rehabilitation exercises being generally tedious to carry out for the user, the setting into place of devices assumed to help him/her should be as simple as possible so as not to discourage him/her and to allow observance of the prescribed and required rehabilitation.

Another drawback of this device is that the information displayed on the viewing screen is not sufficiently intuitive so as to allow him/her to correctly correct his/her posture. Notably, the observation of his/her tilt relatively to the vertical may incite the user to force on his/her muscles excessively for aligning his/her back on the vertical. Now, studies have shown that the level of difficulty of rehabilitation exercises should be progressive and that excessive rehabilitation may have adverse consequences. For example, knee flexure exercises according to a too-large angle after surgery of crossed ligaments may induce an irreversible degradation of the properties of the ligaments.

Further another drawback of this device is that the pieces of information displayed on the screen do not allow the user to apprehend his/her progression during his/her rehabilitation. Indeed, even if the display of a deviation angle value is a piece of relevant information for a practitioner, it is not for a layman user. Finally, the device described in WO 2008/132324 does not allow adaptation of the rehabilitation exercises according to the user.

U.S. Patent Publication No. 2011/0021318 describes a device for training the motor control of a user. U.S. Pat. No. 7,867,140 describes a device for correcting the motor coordination of a user. These devices have the same drawbacks as the device described in WO 2008/132324.

An aim of the present invention is to propose a device and a method giving the possibility of overcoming at least one of the aforementioned drawbacks.

SUMMARY

For this purpose, the invention proposes a method for measuring, monitoring, controlling, evaluating and/or correcting proprioceptive and/or postural and/or locomotor and/or motor and/or spatial orientation abilities of a user, said method being applied in a mobile terminal, the method comprising the following steps:

the reception of a plurality of groups of values measured by sensors, each group comprising values measured at a respective instant of a time period, the determination by processing means of the mobile terminal, of a datum estimated for each group of values, so as to obtain a sequence of data estimated at different instants of the time period, said sequence being representative of an effective movement or of an effective posture of the user during the time period, comparison of each estimated datum with at least one theoretical datum, so as to obtain a plurality of representative matching deviations of variation over time between the effective movement or the effective posture of the user and a desired movement or a desired posture which the user should have achieved, sending the user a piece of information relating to his/her effective movement or his/her effective posture, the calculation of a score according to the plurality of obtained deviations, and the modification of said and at least one theoretical datum according to the calculated score.

In other words, the invention relates to a method for measuring, monitoring, controlling, evaluating and/or correcting (proprioceptive and/or postural and/or locomotor and/or motor and/or spatial orientation) abilities of a user during the execution of an exercise, the method comprising steps of:

measuring and processing in order to detect an effective movement (an effective posture respectively) achieved by the user, comparing the effective movement (of the effective posture respectively) to a theoretical movement (to a theoretical posture respectively), biological feedback-control in order to allow the user to correct his/her effective movement (his/her effective posture, respectively) so as to have it correspond at best to the theoretical movement (to the theoretical posture respectively), calculating a score depending on the result of the comparison, and storing the calculated score, optionally transmitting the score to a third party in order to allow the latter to monitor the development of the performances of the user, and automatically or non-automatically updating a difficulty level of the exercise.

Preferred but non-limiting aspects of the method according to the invention are the following:

the step for sending to the user a piece of information comprises for each deviation, the emission of at least one stimulus by alarm means of the terminal if said deviation exceeds a tolerance threshold, the stimulus alerting the user that the effective movement or the effective posture is too different from the desired movement or from the desired posture, and giving him an indication on modifications to be brought to the effective movement or to the effective posture for reducing the correspondence deviation, the mobile terminal comprises three three-axial sensors consisting in a magnetometer, an accelerometer and a gyroscope, the step for measuring a plurality of groups of values consisting for each group of values to be measured of:

at least one linear acceleration with the accelerometer and preferably three linear accelerations along three orthogonal axes, at least one angular velocity with the gyroscope, and preferably three angular velocities along the three orthogonal axes, at least one magnetic field with the magnetometer, and preferably three magnetic fields along the three orthogonal axes, the step for determining an estimated datum comprises the determination of an orientation vector of the mobile terminal from each group of values stemming from measurements of the accelerometer, and/or of the magnetometer and/or of the gyroscope, the method comprises before the determination step, a step for filtering groups of values by using a Kalman filter so as to remove from said values perturbations due to noises and to measurement errors, the filtering step comprises, for each group of values, the sub-steps consisting of:

estimating a first orientation vector from measurements of the accelerometer and of the magnetometer, estimating a second orientation vector from the measurements of the gyroscope, comparing the first and second estimated orientation vectors and using their difference for updating the Kalman filter.

the method further comprises a step for transmitting the calculated score, in the method:

the estimated data comprise information relative to positions and/or orientations of at least one point of the user at the respective instants of the time period, and said at least one theoretical datum comprises a piece of information relative to a theoretical position and/or a maximum and/or minimum theoretical orientation for said point, in the method:

the estimated data comprise pieces of information relative to displacement velocities and/or accelerations of at least one point of the user at respective given instants of the time period, and at least one theoretical datum comprises a piece of information relative to a displacement velocity and/or to a maximum and/or minimum acceleration of said point.

The invention also relates to a computer programme product comprising a programme code recorded on a computer-readable medium for executing the method according to any of the preceding claims when the computer programme is applied to a computer so as to be executed. The invention also relates to a mobile terminal comprising at least one processor, at least one sensor and at least alarm means, in order to allow measurement, monitoring, control, evaluation and/or correction of proprioceptive and/or postural and/or locomotor and/or motor and/or spatial orientation abilities of a user, characterised in that the processor is programmed for:

receiving a plurality of groups of values measured by at least one sensor, each group comprising measured values at a respective instant of a time period, determining an estimated datum for each group of values, so as to obtain a sequence of estimated data at different instants of the time period, said sequence being representative of an effective movement or of an effective posture of the user during the time period, comparing each estimated datum with at least one theoretical datum, so as to obtain a plurality of representative correspondence deviations of variations over time between the effective movement and the effective posture of the user and a desired movement or a desired posture which the user should have achieved, controlling the emission to the user of a piece of information relating to his/her effective movement or his/her effective posture, calculating a score according to the plurality of obtained deviations, and modifying said and at least one theoretical datum according to the calculated score.

BRIEF DESCRIPTION OF THE DRAWINGS

Other advantages and features will become better apparent from the description which follows of several alternative embodiments, given as non-limiting examples, from the appended drawings wherein.

DETAILED DESCRIPTION

Figure 1:
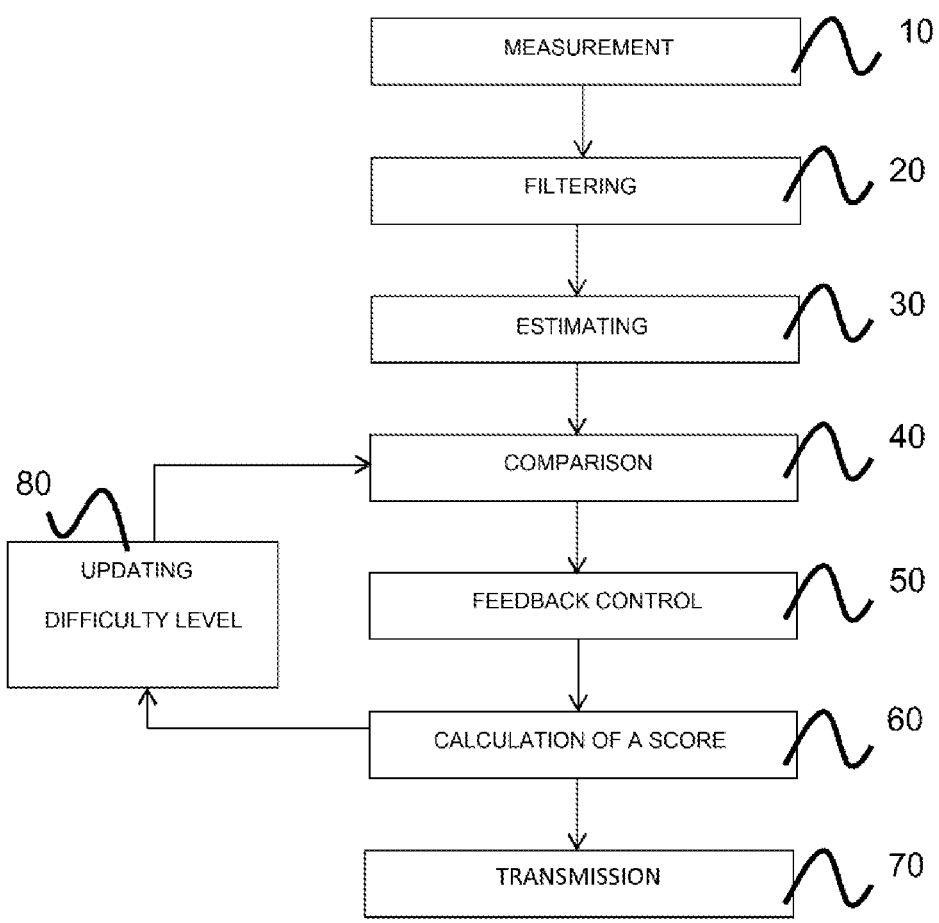
FIG. 1 schematically illustrates an example of a method giving the possibility of controlling, correcting and evaluating postural, locomotor or motor abilities of a user.
Figure 2:
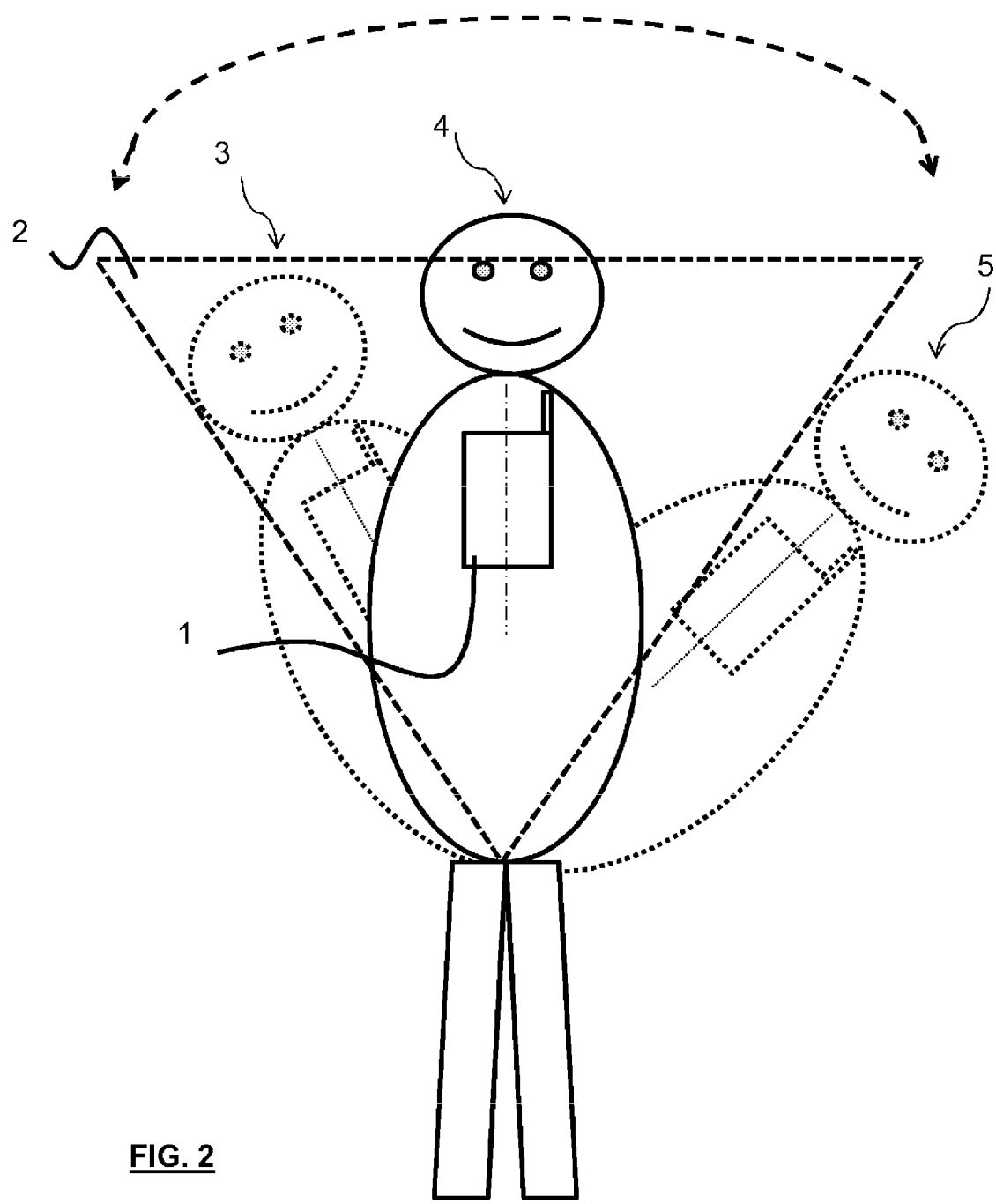
FIG. 2 illustrates an example of use of a mobile terminal programmed for applying the method illustrated in FIG. 1.

Preferred aspects but non-limiting aspects of the present invention will now be described in more detail with reference to FIGS. 1 and 2.

1. General Principles

The method according to the invention is dedicated to the evaluating, to monitoring and to rehabilitation of proprioceptive and/or postural and/or locomotor and/or motor and/or spatial orientation abilities of a user. It may be implemented as a downloadable application able to be applied in a mobile terminal 1 comprising:

processing means such as a processor, measurement means such as sensors, notably an accelerometer, and/or a magnetometer and/or a gyroscope and/or a camera and/or a still camera and/or a microphone and/or any other sensor known to one skilled in the art and which may be contained for example in a mobile phone, tactile and/or visual and/or audio alarm means, such as a vibrator and/or a display screen and/or a loudspeaker, means for transmitting/receiving signals such as an antenna for communicating with other fixed or mobile terminals in order to exchange information with third parties.

The mobile terminal 1 also comprises storage means such as a memory for storing predefined exercises allowing rehabilitation of the user. The fact that the different means for implementing the method are loaded on board a single device such as a mobile terminal 1 facilitates the application of the method for the user. Indeed, the only operation to be carried out for the user is to attach the mobile terminal 1 on him/her, for example by means of a belt comprising a sheath intended to receive the mobile terminal 1. The mobile terminal 1 is for example a mobile phone notably of the Smartphone type, a personal assistant (or "PDA", acronym of the expression "Personal Digital Assistant"), or any type of mobile terminal known to one skilled in the art, such as a connected watch of the iWatch® type.

Thus, an integrated solution is proposed for controlling, correcting and evaluating the motor abilities of a user and thereby allowing his/her rehabilitation from a mobile terminal positioned:

on the patient or at a distance from the patient, notably depending on the exercises to be carried out.

For example for applying certain exercises, the mobile terminal may be attached on a mobile platform on which the user stands while trying to be immobile; the terminal then measures the movement of the platform: the less the platform oscillates, better is the performance of the user.

For the application of other exercises, the mobile terminal may be attached on a region of the user. Of course, the region in which the mobile terminal is attached depends on the body segment, or more widely on the ability of rehabilitation. For example, for rehabilitation of the sensor-motor and functional abilities of the lumbar rachis, the mobile terminal will be attached on the thorax cage of the user. For rehabilitation of the sensor-motor and functional abilities of the elbow, the mobile terminal will be attached on the forearm of the user, etc.

Moreover for the rehabilitation of a given body segment, the region in which is fixed the mobile terminal may vary depending on the exercise carried out. For example in the case of rehabilitation of the sensor-motor and functional abilities of the knee, the mobile terminal may be attached:

on the thigh of the user during completion of a first exercise, and on the calf of the user during the completion of a second exercise, etc.

2. Method

We shall now describe an example of a method with reference to the rehabilitation of the joint of the elbow of a user. It is assumed that the user has attached beforehand the mobile terminal on his/her forearm, and has selected an exercise. Advantageously, the user may be accompanied during these steps for setting into place the terminal and for selecting an exercise. For example, a first phase of the method may consist of informing the user on an operating procedure helping him/her to set into place the terminal and to select an exercise. This information phase may for example consist in the addition of a visual and/or audio tutorial to the user. Also, a visual and/or audio description of the exercise to be carried out may be provided to the user.

Once the exercise has been selected, the mobile terminal 1 executes different phases:

for detecting the effective movement carried out by the user, comparing it with a theoretical movement that the user should carry out "ideally", optionally emit alarms for allowing the user to correct his/her effective movement so as to have it correspond at best with the theoretical movement, calculating a score for the exercise, notably depending on the deviation between the effective and theoretical movements, updating the difficulty level of the exercise and/or adding or suppressing an exercise, and optionally sending the calculated score to a third party in order to allow him/her to follow the development of the rehabilitation or of the training and/or ensuring observance of the treatment or of the managing.

Thus, not only the user is assisted for allowing him/her to correctly carry out a series of prescribed exercises, but in addition he/she may assess his/her progress by means of the quantification associated with the exercise carried out. This quantification further allows updating of the difficulty levels of the exercises in order to optimise the effects of the rehabilitation and to inform third parties on the observance of the treatment and on the development of this rehabilitation. These different phases will now be described in more detail with reference to the method illustrated in FIG. 1.

2.1 Measurement of Groups of Values

In one step, the method comprises the measurement 10 with sensors of the mobile terminal 1, of a plurality of groups of values. Each value of a group stems from a respective sensor. For example, in the case of a mobile terminal comprising an accelerometer 3D, a 3D magnetometer and a 3D gyroscope:

three values corresponding to linear accelerations along three orthogonal axes, three values correspond to angular velocities along the same three orthogonal axes, and three values correspond to magnetic fields along the same three orthogonal axes.

Of course, the present invention is not limited to the use of a 3D accelerometer, a 3D magnetometer and a 3D gyroscope, but relates to the use of any type of accelerometer, magnetometer and gyroscope (notably 1D, 2D). The use of groups of values each comprising measurements stemming from an accelerometer, a magnetometer and a gyroscope gives the possibility of improving the accuracy in estimating the effective movement performed by the user.

2.2 Filtering of the Measured Values

The method may also comprise an optional filtering step 20 for groups of values measured from sensors of the mobile terminal. This gives the possibility of suppressing the perturbations due to noises and measurement errors. Advantageously, the filtering of the groups of values may be applied by using a Kalman filter.

This type of filter is particularly suitable for estimating parameters of a system changing over time from noisy measurements, which is the case within the scope of the invention since the different groups of values are representative signals of a movement performed by the user. Thus, each group of values bears information on:

the position of the mobile terminal at a given instant, the orientation of the mobile terminal at the given instant, and the displacement velocity of the mobile terminal at the given instant.

From these pieces of information relative to the mobile terminal, it is possible to infer therefrom the movement of one (or several) point(s) of the relevant body segment (here the forearm of the user).

2.3 Determination of Estimated Data

During another step, the method comprises the determination 30 of one (or several) data estimated from each group of values. More specifically, the processor of the mobile terminal treats the groups of values for extracting the pieces of information relative to the position, and/or the orientation and/or the velocity and/or the acceleration of the displacement of the mobile terminal at different measurement instants of the time period. A sequence of estimated data is thereby obtained at different instants of the time period, this sequence being representative of the effective movement of the user during the time period.

Depending on the type of exercise, only certain parameters of the movement performed by the user may require a control. For example for certain exercises, the displacement velocity of the body segment is not a determining criterion of the rehabilitation. In this case, no estimated datum relative to the displacement velocity will be determined from groups of values. This gives the possibility of limiting:

the material resources used (notably memory space), the consumed energy by the mobile terminal for applying the method.

2.4 Comparison of the Estimated Data with Theoretical Data

In another step, the sequence of estimated data is compared 40 with theoretical data. These theoretical data are representative of a desired movement which the user will have to perform during the execution of the exercise. Depending on the type of exercise and on its difficulty level, the nature of the theoretical data may vary.

For example, if one considers an exercise consisting for the user of laying his/her elbow on a stable support and of moving his/her forearm between a horizontal position and a vertical position, then the sequence of estimated data may be compared:

to a single theoretical datum corresponding to a maximum displacement velocity of the forearm of the user, with two theoretical data respectively corresponding to a minimum velocity and to a maximum displacement velocity of the forearm of the user, with three theoretical data corresponding to minimum and maximum displacement velocities and to an angle of more than 90° between the extreme positions occupied by the forearm of the user, etc.

The comparison step gives the possibility of obtaining a plurality of correspondence deviations.

2.5 Feedback Control

Each calculated correspondence deviation is representative of a variation, at a given instant, between the effective movement of the user and the desired movement which the user would have to perform. Therefore, each of the calculated deviations are compared 50 with a tolerance threshold (which notably depends on the difficulty level of the exercise) for determining whether the user has to be alerted or not that his/her movement is incorrect. The deviations are not necessarily related to an inability of the user of correctly performing the "ideal" movement, but may come from the fact that the user has difficulty in evaluating certain constraints which may be quantified with difficulty on his/her movement such as the displacement velocity.

This is why in addition to the fact of alerting the user that his/her effective movement is incorrect, the invention proposes providing him with an indication which will allow him/her to correct his/her effective movement in order to have it better match the "ideal" movement. This indication is provided to the user by means of the emission of one (or several) stimuli either visual and/or audio and/or tactile. Advantageously, the biological feedback control may consist in emitting stimuli of different types depending on the nature of the error to be corrected (in the movement performed by the patient) and/or depending on the preferences or abilities of his/her user: for example a deaf user may select one (or several) visual and/or tactile stimuli.

For example:

if the user performs the movement according to the proper angle but at a too high velocity, the feedback control may consist in emitting an audio stimulus, while if the user performs the movement at the right speed but with a poor angle, the feedback control will consist in emitting an audio stimulus (if the angle is too small) or tactile (if the angle is too large).

Also more or less rapid successions (or more or less numerous) of stimuli of the same nature may be used for indicating to the user that a parameter of his/her movement is incorrect.

For example, a rapid (respectively slow) succession of audio stimuli may be used for indicating a too slow displacement velocity (too rapid respectively) of the forearm (or vice versa).

2.6 Calculation of a Score, Updating and Transmission

In another step, the method comprises the calculation 60 of a score associated with the execution of the exercise by the user. The calculation of this score has many advantages. Indeed, it allows the user to evaluate his/her progression in the execution of the exercises, and therefore the benefits of his/her rehabilitation. It also gives the possibility of updating 80 the rehabilitation of the user, notably by updating the tolerance threshold (increase in the threshold if the score is low or decrease of the threshold if the score is high), and therefore an updating of the difficulty level of the exercises to be executed. Finally, when the method comprises a transmission step 70 of the score(s), the calculation of the score allows a third party to follow the progress of the user in his/her rehabilitation.

3. Examples of Use 3.1 Rehabilitation of Proprioceptive Abilities

The following example relates to a mobile application dedicated to the evaluating, monitoring and rehabilitation of proprioceptive abilities of a user. It consists in an integrated solution of measurements of the angle of at least one joint or of at least one body segment (for example, ankle, knee, hip, spine, wrist, arm, shoulder, neck) during predefined exercises. This application gives the possibility of both measuring and improving the proprioceptive abilities by means of a visual and/or audio and/or tactile biological feedback control (for example, vibratory). The communicating nature of the mobile terminal may be used for transmitting the obtained results to the relevant third parties (physician, physiotherapist, etc.).

Functionality

The application gives the possibility of quantifying the movements of the joint from measurements stemming from the sensors loaded on board the mobile terminal, and notably:

a 3D accelerometer for measuring linear accelerations along three orthogonal axes, a 3D gyroscope for measuring angular velocities along the same three orthogonal axes, and a 3D magnetometer for measuring magnetic fields along the same three orthogonal axes.

The application was designed so as to be used autonomously and includes pre-programmed training exercises. A portion of these exercises is dedicated to rehabilitation and is based on the principle of perceptual supplementation. To do this, an audio or vibratory feedback control was programmed for alerting the user of a too large tilt relatively to the expected state and for inciting him/her to reposition himself/herself correctly.

One of the originalities of this exemplary embodiment lies on the integration of the information stemming from the gyroscope and the magnetometer which give the possibility of improving the quality in the estimation of the movement performed by the user. Another originality of this exemplary embodiment lies on the design of a mobile application dedicated to the evaluating and to the rehabilitation with a mobile terminal as a single support.

Evaluating

It is assumed in the following that a smartphone is used comprising three types of three-axes sensors: an accelerometer, a magnetometer and a gyroscope. The obtained measurements are subject to biases specific to each of the three types of sensors (noise, magnetic perturbation, drift due to integration). This is why they are used in a complementary way in an extended Kalman filter for correcting the biases of the gyroscope and for reliably estimating orientations.

The tilt angles ($\theta$, $\varphi$) are estimated from measurements from the accelerometer. The direction ($\psi$) is estimated from measurements from the magnetometer. A first estimation of the orientation vector ($\varphi$, $\theta$, $\psi$) is thereby obtained. In parallel, an estimation of these same angles is obtained from the gyroscope giving rise to a second estimation of the orientation vector ($\varphi_g$, $\theta_g$, $\psi_g$).

The various perturbations of the gyroscopic measurements are corrected by comparing both estimations obtained for the orientation vector. The difference ($\varphi_{diff}$, $\theta_{diff}$, $\psi_{diff}$) between the first and second estimated orientation vectors is then used for updating the coefficients of the Kalman filter which will be applied in the following iteration. Finally, the merging of the data from the various sensors provides an estimation of the angles of rotation ($\varphi_{est}$, $\theta_{est}$, $\psi_{est}$) representing the angle of the mobile terminal relatively to its average position over the first "n" (for example five) seconds of the test (reference ($\varphi_0$, $\theta_0$, $\psi_0$)). Perceptual supplementation and biofeedback The application proposes, in addition to the evaluating, rehabilitation exercises based on the application and the use of sensorial biological feedback control. Advantageously, the biological feedback control may consist in the emission of stimuli for which the type (for example, sensorial, audio, tactile) may vary depending on the sensitivity, on the abilities and/or on the preferences of the user. For example, visual stimuli will be avoided for blind or visually impaired, etc. Alternatively, biological feedback control may consist in the combination of different types of stimuli: for example visual/audio and audio/tactile, etc.

Moreover, the operating principle of biological feedback control may vary according to the user. For example biological feedback control may be:

continuous; in this case, the user has a continuous return on the present positions of his/her joint, or intermittent (repulsive or attractive); in this case, the user receives pieces of information relative to the deviation (or the direction and/or amplitude error) between the present position of his/her joint and that which would be obtained considering the proposed exercise. In other words in this case, there is no error, there is no sensorial feedback.

Advantageously, a tolerance level a so called "white area" level 2, which may be parameterised, is proposed in order to adapt the difficulty level to the motor abilities of the user and to his/her progression, notably.

In the following an application dedicated to the rehabilitation of the lumbar rachis is considered. The user is provided with 4 vibrators positioned on his/her body, on the front, rear, right and left faces. He/she should move his/her torso in the four directions, according to a programme of proposed exercises.

Two alternatives of biological feedback control, may at least for example be proposed:

i) a first alternative (a so called "attractive cuing") wherein the user has the instruction of moving his/her torso in the direction of the vibration; for example if the rachis is on the left relatively to the white area (position referenced as 5 in FIG. 2), the right vibrator is enabled; the user moves his/her torso to the right; the vibration stops when the tilt of the torso is again inside the white area 2 (for example positions referenced as 3 and 4 in FIG. 2), i.e. when the tilt of the torso is the one "requested" by the exercise;

ii) a second alternative (a so called "repulsive cuing") in which the user has the instruction of moving his/her torso in the direction opposite to the vibration; for example, if the torso of the user is on the left relatively to a dead area, the left vibrator is enabled; the user moves his/her torso to the right; the vibration stops when the tilt of the torso is again inside the white area, i.e. when the tilt of the torso is the one "requested" by the exercise.

Of course, one skilled in the art will have understood that other alternatives of biological feedback control are possible.

Definitively, all the interest of the invention is to position an all-in-one device, grouping functionalities for measurement, analysis, storage, correction, sensorial return and adaptation. This device, because of its communicating nature, gives the possibility of getting back very rapidly to information for a third party (for example a medical team), so as to verify the results and the performed exercises, and in the long run, adapting the sessions proposed to the user. Another functionality of the invention lies in the secured transmission of the measured and analysed data and their comparison with a database.

3.2. Rehabilitation of Abilities for Controlling the Posture, the Balance and the Gait The following example relates to a mobile application dedicated to the evaluating, to the monitoring, to the training and to the rehabilitation of the control abilities for posture, balance and gait. This application consists in an integrated solution of measurements and feedback action on positions and/or velocities and/or accelerations and/or orientations of one or several body segments (for example the angle of the torso relatively to the vertical) in postural, motor and locomotor tasks which the user may advantageously perform in his/her living quarters (and not only in a medical or paramedical office). According to the needs, this solution may also integrate relevant complementary measurements (such as kinematic measurements and/or kinetic measurements and/or physiological measurements) by means of wired sensors or wireless sensors connected to the mobile terminal (such as heart rate sensors and/or breath rate sensors and/or pressures and/or oculometry and/or electromyography and/or GPS localisation, etc.).

The centralisation of the data by the mobile terminal gives the possibility of coordinating and synchronizing the acquisitions and of merging these pieces of individual information in order to access information of a higher level. The tasks for evaluating and/or the training or rehabilitation exercises may for example consist of standing up as immobile as possible in different postural conditions (for example on different types of stable or unstable supports, and/or in different sensorial environments). Other conditions may be applied by means of wireless actuators connected to the mobile terminal (e.g. fatigue or perturbation effect by a vibrator, change in the visual conditions with spectacles connected to augmented reality such as "Google Spectacles" (or "Google Glasses®"), movements induced by a platform).

This application allows both:
i) acquisition of an objective, quantitative and automatic measurement of the proprioceptive abilities for controlling the posture, the balance and the locomotion and the spatial orientation and
ii) improvement of these abilities by means of the use of a biological feedback control (or "biofeedback").

For example, a biological feedback of the type
audio (via speakers), and/or
visual (via connected spectacles or a display screen) and/or further
tactile (via a mechanical oscillating system such as a vibrator)

may be provided to the user in real time for informing him/her on his/her postural present condition; alternatively, the provision of the biofeedback to the user may be deferred, for example at the end of an exercise.

This biological control feedback may for example be triggered in real time as soon as a postural instability situation is established, with reference to a predefined model or to the abilities of the user determined during a learning phase. It may for example be triggered from measurements of displacements of the torso in order to alert the user of a too large tilt of his/her torso relatively to its initial condition and inciting him/her to be correctly repositioned. Several parameterisations may be used by the biofeedback system depending on the needs of the user and/or on prescriptions from a practitioner (physician, physiotherapist, rehabilitation therapist, etc.).

Depending on the difficulty level of each exercise, the biofeedback triggering may be accomplished:
continuously; in this case, a biofeedback is enabled as soon as the effective movement of the user differs from the theoretical movement (or by a reference value such as a maximum tilt which should not be exceeded, or a maximum velocity, etc.),
discontinuously; in this case, a biological feedback control is enabled when the effective movement of the user differs from the theoretical movement to within a tolerance margin (predefined thresholds).

In every case, the difficulty of each exercise may be parameterised in order to take into account the abilities of the user. Advantageously, the difficulty level may be updated (notably increased) for taking into account the progress of the user during his/her rehabilitation. One of the originalities of the present invention lies on the design of a mobile application dedicated to the evaluating and to the rehabilitation with a mobile terminal as a single support.

The acquisition, the processing, the analysis of the data, the generation of a biological feedback and the activation of actuators are entirely controlled and managed by the mobile terminal. Indeed, the latter is used like a control platform giving the possibility of receiving signals, of processing them, of storing them and of emitting pieces of information. Actuators may be connected for varying the conditions of use and being directly enabled from the mobile terminal depending on the exercise and on the sought difficulty level.

The activation of these additional tools may depend and be modulated by the reactivity of the subject to the different stimulations relatively to the data sensed by the mobile terminal. The use of additional sensors gives the possibility of accessing complementary information which when they are merged become information of a high level. The centralisation, the merging and the activation of certain actuators in response to this new flow of information are there again carried out from a single mobile terminal. The proposal of exercises and the modulation of their difficulty level are automatically generated by the mobile terminal depending on the present condition of the user and of his/her progression. Advantageously, the communicating nature of the mobile terminal may be used for transmitting obtained results to relevant third parties (physician, physiotherapist, trainer, social networks, etc.).

Postural and Locomotor Evaluating

The mobile terminal used in the example described hereafter is a smartphone comprising three types of three-axis sensors: an accelerometer, a magnetometer and a gyroscope. The obtained measurements are subject to the biases specific to each of these types of sensor (e.g. noise, magnetic perturbations, drift due to the integration). These measurements are used in a complementary manner with a Kalman filter for correcting the biases of the gyroscope and for reliably estimating the orientation of the support on which stands the user (for example, unstable platform or Freeman plate) and/or of a body segment of the user (for example, the torso or the lower or upper limb).

The filter used is an extended Kalman filter. The merging of the data from the different sensors provides an estimation of the angles of rotation representing the angle of the smartphone relatively to its average position on the first "n" seconds of the test ("n" being an integer greater than or equal to zero). Training/rehabilitation based on the use of biofeedback The application further proposes from the evaluating of the proprioceptive abilities, of the control of the posture, of the balance and of the locomotion, rehabilitation exercises based on the use of visual and/or audio and/or tactile biofeedback. Various methods for generating the biofeedback are possible and may be parameterized. For example, in the case of the rehabilitation of proprioceptive abilities of the torso, as soon as the user has a too large angle and leaves a tolerance area or "white area", a sensorial signal is sent to the corresponding actuator, on the incriminated side. Alternatively, this sensorial signal may be sent to the actuator oppositely to the incriminated side, according to the preferences of the user and/or of medical prescriptions, etc.

In every case, this signal is an additional piece of sensorial information on which the user may be based. The tolerance level of the "white" area is an adjustable parameter from the interface of the smartphone in order to adapt the difficulty level to the physical condition of the user (in this case, proprioceptive abilities) and to the progression of this physical condition (and/or to the medical prescriptions).

The invention claimed is:

1. A method for measuring, monitoring, controlling, evaluating and/or correcting proprioceptive and/or postural and/or locomotor and/or motor and/or spatial orientation abilities of a user, the method being applied in a mobile terminal, the method comprising the following steps:
    receiving a plurality of measured groups of values by sensors, each group comprising measured values at a respective instant of a time period;
    determining by a processor of the mobile terminal, an estimated datum for each group of values, so as to obtain a sequence of data estimated at different instants of the time period, the sequence being representative of an effective movement or of an effective posture of the user during the time period;
    comparing each estimated datum with at least one theoretical datum so as to obtain a plurality of representative correspondence deviations of the variations over time between the effective movement or the effective posture of the user and a desired movement or a desired posture which the user should have achieved;
    sending to the user a piece of information relating to his/her effective movement or his/her effective posture;
    calculating a score according to the plurality of obtained deviations; and
    modifying the at least one theoretical datum depending on the calculated score;
    wherein the step for sending to the user the piece of information comprises, for each deviation, the emission of at least one stimulus by an alarm of the terminal if the deviation exceeds a tolerance threshold, the stimulus alerting the user that the effective movement or the effective posture is too different from the desired movement or from the desired posture, and giving him/her an indication on modifications to be brought to the effective movement or to the effective posture for reducing the correspondence deviation.

2. The method according to claim 1, wherein the step for measuring a plurality of groups of values include for each group of values to be measured:
    at least one linear acceleration by a three-axis accelerometer of the mobile terminal;
    at least one angular velocity by a three-axis gyroscope of the mobile terminal; and
    at least one magnetic field by a three-axis magnetometer of the mobile terminal.

3. The method according to claim 2, wherein the step for determining an estimated datum comprises the determination of an orientation vector of the mobile terminal from each group of values stemming from the measurements of the accelerometer, and/or of the magnetometer and/or of the gyroscope.

4. The method according to claim 2, further comprising before the determination step, a filtering step of the groups of values by using a Kalman filter so as to remove the values of the perturbations due to noises and to measurement errors.

5. The method according to claim 4, wherein the filtering step comprises, for each group of values, the sub-steps comprising:
    estimating a first orientation vector from measurements of the accelerometer and of the magnetometer;
    estimating a second orientation vector from measurements of the gyroscope; and
    comparing the first and second estimated orientation vectors and using their difference for updating the Kalman filter.

6. The method according to claim 1, which further comprises a step for transmitting the calculated score.

7. The method according to claim 1, wherein:
    the estimated data comprise pieces of information relative to positions and/or orientations of at least one point of the user at respective instants of the time period; and
    the at least one theoretical datum comprises a piece of information relative to a theoretical position and/or a maximum and/or minimum theoretical orientation for the point.

8. The method according to claim 1, wherein:
    the estimated data comprise pieces of information relative to displacement velocities and/or accelerations of at least one point of the user at respective given instants of the time period; and
    the at least one theoretical datum comprises a piece of information relative to a displacement velocity and/or to a maximum and/or minimum acceleration of the point.

9. The method according to claim 1, wherein:
    wherein the estimated data comprise pieces of information relative to displacement velocities and/or accelerations of at least one point of the user at respective given instants of the time period, the at least one theoretical datum comprises a piece of information relative to a displacement velocity and/or to a maximum and/or minimum acceleration of the point, and
    wherein the at least one theoretical datum is increased if the calculated score is below a predetermined value and wherein the at least one theoretical datum is decreased if the calculated score is above a predetermined value.

10. A computer program product comprising a program code recorded on a computer-readable medium for executing:
- a receipt of a plurality of measured groups of values by sensors, each group comprising measured values at a respective instant of a time period;
- a determination of an estimated datum for each group of values, so as to obtain a sequence of data estimated at different instants of the time period, the sequence being representative of an effective movement or of an effective posture of a user during the time period;
- a comparison of each estimated datum with at least one theoretical datum so as to obtain a plurality of representative correspondence deviations of the variations over time between the effective movement or the effective posture of the user and a desired movement or a desired posture which the user should have achieved;
- sending to the user a piece of information relating to his/her effective movement or his/her effective posture;
- a calculation of a score according to the plurality of obtained deviations; and
- a modification of the at least one theoretical datum depending on the calculated score;
- wherein the computer program is applied to a computer so as to be executed thereon; and
- wherein the sending to the user the piece of information comprises, for each deviation, the emission of at least one stimulus by an alarm of the terminal if the deviation exceeds a tolerance threshold, the stimulus alerting the user that the effective movement or the effective posture is too different from the desired movement or from the desired posture, and giving him/her an indication on modifications to be brought to the effective movement or to the effective posture for reducing the correspondence deviation.

11. The computer program product according to claim 10, wherein:
- wherein the estimated data comprise pieces of information relative to displacement velocities and/or accelerations of at least one point of the user at respective given instants of the time period, the at least one theoretical datum comprises a piece of information relative to a displacement velocity and/or to a maximum and/or minimum acceleration of the point, and
- wherein the at least one theoretical datum is increased if the calculated score is below a predetermined value and wherein the at least one theoretical datum is decreased if the calculated score is above a predetermined value.

12. A device comprising a mobile terminal and sensors, the device:
- receiving a plurality of measured groups of values by the sensors, each group comprising measured values at a respective instant of a time period;
- determining by a processor of the mobile terminal, an estimated datum for each group of values, so as to obtain a sequence of data estimated at different instants of the time period, the sequence being representative of an effective movement or of an effective posture of a user during the time period;
- comparing each estimated datum with at least one theoretical datum so as to obtain a plurality of representative correspondence deviations of the variations over time between the effective movement or the effective posture of the user and a desired movement or a desired posture which the user should have achieved;
- sending to the user a piece of information relating to his/her effective movement or his/her effective posture;
- calculating a score according to the plurality of obtained deviations; and
- modifying the at least one theoretical datum depending on the calculated score;
- wherein the sending to the user the piece of information comprises, for each deviation, the emission of at least one stimulus by an alarm of the terminal if the deviation exceeds a tolerance threshold, the stimulus alerting the user that the effective movement or the effective posture is too different from the desired movement or from the desired posture, and giving him/her an indication on modifications to be brought to the effective movement or to the effective posture for reducing the correspondence deviation.

13. The device according to claim 12, wherein:
- wherein the estimated data comprise pieces of information relative to displacement velocities and/or accelerations of at least one point of the user at respective given instants of the time period, the at least one theoretical datum comprises a piece of information relative to a displacement velocity and/or to a maximum and/or minimum acceleration of the point, and
- wherein the at least one theoretical datum is increased if the calculated score is below a predetermined value and wherein the at least one theoretical datum is decreased if the calculated score is above a predetermined value.

* * * * *